US012790660B2

(12) United States Patent
Cui et al.

(10) Patent No.: US 12,790,660 B2
(45) Date of Patent: Nov. 10, 2026

(54) THIODIGLYCOLAMIC ACID EXTRACTANT, AND PREPARATION METHOD AND USE THEREOF

(71) Applicant: INSTITUTE OF APPLIED CHEMISTRY, JIANGXI ACADEMY OF SCIENCES, Nanchang (CN)

(72) Inventors: Hongmin Cui, Nanchang (CN); Jinsong Shi, Nanchang (CN); Nanfu Yan, Nanchang (CN); Yuewei Liu, Nanchang (CN); Yaqing Weng, Nanchang (CN); Chaoyang Deng, Nanchang (CN)

( * ) Notice: Subject to any disclaimer, the term of this patent is extended or adjusted under 35 U.S.C. 154(b) by 573 days.

(21) Appl. No.: 18/253,740

(22) PCT Filed: Feb. 21, 2023

(86) PCT No.: PCT/CN2023/077324
§ 371 (c)(1),
(2) Date: May 19, 2023

(87) PCT Pub. No.: WO2023/241087
PCT Pub. Date: Dec. 21, 2023

(65) Prior Publication Data

US 2024/0368726 A1 Nov. 7, 2024

(30) Foreign Application Priority Data

Jun. 16, 2022 (CN) ......................... 202210677900.4

(51) Int. Cl.
*C22B 3/32* (2006.01)
*C07C 323/52* (2006.01)
(Continued)

(52) U.S. Cl.
CPC .............. *C22B 3/32* (2021.05); *C07C 323/52* (2013.01); *C22B 11/04* (2013.01); *C22B 13/04* (2013.01);
(Continued)

(58) Field of Classification Search
CPC ........... C22B 3/32; C22B 11/04; C22B 13/04; C22B 15/0084; C22B 23/0453; C22B 26/22; C07C 323/52
See application file for complete search history.

(56) References Cited

U.S. PATENT DOCUMENTS

2019/0287691 A1* 9/2019 Abergel ................. G21C 19/46

FOREIGN PATENT DOCUMENTS

CN 103068792 A 4/2013
CN 103509947 A 1/2014
(Continued)

OTHER PUBLICATIONS

Suneesh, A. S. "Development of Extractants for the Mutual Separation of Lanthanides and Actinides." Thesis. Homi Bhabha National Institute. See pp. xiii, 83, and 85. (Year: 2011).*
(Continued)

*Primary Examiner* — Tima M. McGuthry-Banks

(57) ABSTRACT

The present disclosure provides a thiodiglycolamic acid extractant, and a preparation method and use thereof, belonging to the technical fields of extractant synthesis and extraction separation in the field of hydrometallurgy. In the present disclosure, the preparation method includes: mixing thiodiglycolic anhydride, an alkyl-substituted secondary amine, and an organic reagent in proportion; subjecting a resulting mixed reactant to a reaction I by stirring in an ice-water bath for 10 min to 60 min, and then to a reaction II by stirring at 20° C. to 50° C. for 6 h to 24 h; after the reaction II is completed, conducting extraction on an
(Continued)

obtained product, and subjecting an obtained organic phase to washing, drying, suction filtration, and rotary evaporation to obtain the extractant.

7 Claims, 8 Drawing Sheets

(51) Int. Cl.

| | |
|---|---|
| ***C22B 3/00*** | (2006.01) |
| ***C22B 11/00*** | (2006.01) |
| ***C22B 15/00*** | (2006.01) |
| ***C22B 26/22*** | (2006.01) |

(52) U.S. Cl.

CPC ...... *C22B 15/0084* (2013.01); *C22B 23/0453* (2013.01); *C22B 26/22* (2013.01)

(56) References Cited

FOREIGN PATENT DOCUMENTS

| | | |
|---|---|---|
| CN | 104524808 A | 4/2015 |
| CN | 104531993 A | 4/2015 |
| CN | 107513614 A | 12/2017 |
| CN | 114853617 A | 8/2022 |
| CN | 115028561 A | 9/2022 |

OTHER PUBLICATIONS

Grimwade, Mark. Introduction to Precious Metals: Metallurgy for Jewelers & Silversmiths. Brynmorgen Press. ISBN: 978-1-929565-30-6. (Year: 2009).*

Helmenstine, Anne Marie, Ph.D. "What Is a Base Metal? Definition and Examples." ThoughtCo. thoughtco.com/base-metal-definition-and-examples-608464. (Year: 2019).*

Satusinprasert, Palakorn et al. Separation of Light and Middle-Heavy Rare Earths from Nitrate Medium by Liquid-Liquid Extraction. Kasetsart Journal (Nat. Sci). 49:1-9. (Year: 2015).*

Suneesh, A. S. "Mutual separation of americium(III) and europium(III) using glycolamic acid and thioglycolamic acid" Radiochimica Acta, vol. 100, No. 7, Mar. 12, 2012, pp. 425-430, see in particular, Figure 1, section 2.1 on p. 426.

Jin, Chang. "Extraction of Ln(III) and An(III) by N, N-di(2-ethylhexyl)-thio-diglycolamic Acid" Solvent Extraction and Ion Exchange, vol. 40, No. 6, Feb. 3, 2022, pp. 641-653.

International Search Report, Chinese Patent Office, Application No. PCT/CN2023/077324, Apr. 13, 2023.

* cited by examiner

THIODIGLYCOLAMIC ACID EXTRACTANT, AND PREPARATION METHOD AND USE THEREOF

CROSS REFERENCE TO RELATED APPLICATION

The present application is a national stage application of International Patent Application No. PCT/CN2023/077324, filed on Feb. 21, 2023, which claims priority to Chinese Patent Application No. CN202210677900.4 filed to the China National Intellectual Property Administration (CNIPA) on Jun. 16, 2022 and entitled "THIODIGLYCOLAMIC ACID EXTRACTANT, AND PREPARATION METHOD AND USE THEREOF", which is incorporated herein by reference in its entirety.

TECHNICAL FIELD

The present disclosure belongs to the technical fields of extractant synthesis and extraction separation in the field of hydrometallurgy, and specifically relates to a thiodiglycolamic acid extractant, and a preparation method and use thereof. The present disclosure particularly relates to use of the extractant in extraction of precious metal ions in an acidic feed liquid.

BACKGROUND

With the rapid development of science and technology, the demand for precious metals is increasing, leading to a rapid increase in the amount of electronic wastes. If being not handled properly, these electronic wastes can cause serious environmental problems. In addition, the electronic waste contains a variety of high-grade precious metal elements, which have a high recycling value. Therefore, the recovery of precious metals from the electronic waste is of great economic and environmental significances.

In precious metal hydrometallurgy, solvent extraction is considered to be the most promising method for recovering precious metals due to its desirable selectivity and high metal recovery. At present, two types of extractants, sulfides and sulfoxides, are mainly used at home and abroad in treating and recovering the precious metals. Neutral thioether extractants have excellent extraction properties for precious metals, and show important application values in extraction chemistry and hydrometallurgy. However, traditional thioether extractants still have poor acid resistance and long extraction equilibrium time, and obviously cannot meet requirements for the extractant of an acid leaching solution system of the electronic waste. Moreover, the traditional extractants still have an unsatisfactory separation effect on precious metals and base metals, and generally require multiple methods to be coupled, resulting in complex treatment processes and high costs. Therefore, it is necessary to develop a new type of efficient precious metal extractant that matches the precious metal.

SUMMARY

In view of this, aiming at the problems or defects in the prior art, an objective of the present disclosure is to provide a thiodiglycolamic acid extractant, and a preparation method and use thereof. The present disclosure intends to solve or at least partially solve the above-mentioned technical defects existing in the prior art.

In the present disclosure, the thiodiglycolamic acid extractant has a simple and easy-to-operate synthesis method, desirable salt tolerance and acid resistance, a high extraction efficiency for precious metal ions, and an excellent selectivity. The extractant can recover precious metal ions from an acidic feed liquid with a short process and a high efficiency, and has a certain industrial application value.

To achieve the above objective, the present disclosure adopts the following technical solutions:

A first aspect of the present disclosure is to provide a thiodiglycolamic acid extractant, where the extractant shows a thiodiglycolamic acid structure, and has a structural formula shown in formula 1:

where $R_1$ and $R_2$ are independently linear or branched alkyl, and there are totally greater than six carbon atoms in $R_1$ and $R_2$.

formula 1

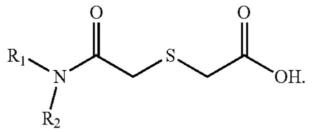

Further, there are totally 7 to 24 carbon atoms in $R_1$ and $R_2$.

A second aspect of the present disclosure is to provide a preparation method of the thiodiglycolamic acid extractant, including the following steps:

mixing thiodiglycolic anhydride, an alkyl-substituted secondary amine, and an organic reagent in proportion; subjecting a resulting mixed reactant to a reaction I by stirring in an ice-water bath for 10 min to 60 min, and then to a reaction II by stirring at 20° C. to 50° C. for 6 h to 24 h; after the reaction II is completed, subjecting an obtained organic phase to washing, drying, and suction filtration; and subjecting an obtained organic phase filtrate to vacuum distillation to remove a solvent, to obtain the thiodiglycolamic acid extractant.

Further, the alkyl-substituted secondary amine has a structural formula shown in formula 2:

formula 2

where $R_1$ and $R_2$ are independently linear or branched alkyl, and there are totally 7 to 24 carbon atoms in $R_1$ and $R_2$.

Preferably, the alkyl-substituted secondary amine is any one selected from the group consisting of diisooctylamine, di-n-octylamine, di-n-hexylamine, and N-methyloctylamine.

Further, the thiodiglycolic anhydride and the alkyl-substituted secondary amine are at a molar ratio of 1:1 to 1:2.

Further, the organic reagent is any one selected from the group consisting of dichloromethane, chloroform, tetrahydrofuran, acetonitrile, N,N-dimethylformamide (DMF), and toluene.

Specifically, there is no specific limitation on a dosage of the organic reagent, as long as the thiodiglycolic anhydride and the alkyl-substituted secondary amine are fully dissolved.

Further, the mixed reactant is subjected to the reaction I by stirring in the ice-water bath for 30 min.

Further, the washing specifically includes: washing the organic phase with a dilute hydrochloric acid solution to remove excess alkyl-substituted secondary amine, and then repeatedly washing with deionized water until a pH value is 3 to 4.

Further, the drying is preferably conducted with anhydrous magnesium sulfate.

Specifically, the thiodiglycolamic acid extractant is prepared by ring-opening, and a specific reaction formula is shown in formula 3:

formula 3

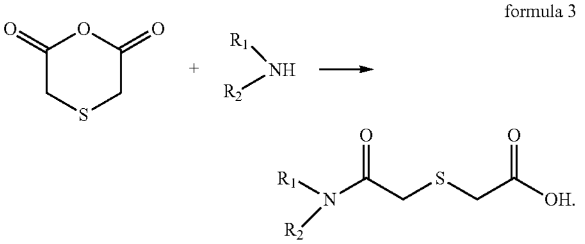

An effect that each of the raw materials plays in the present disclosure and a preparation reaction mechanism are as follows:

The secondary amine attacks the thiodiglycolic anhydride to generate an N-substituted thiodiglycolamic acid; a steric hindrance of the secondary amine directly affects ring-opening destination and a product yield of the thiodiglycolic anhydride.

In addition, in the present disclosure, a purpose of the reaction in the ice-water bath is to prevent the thiodiglycolic anhydride and a secondary amine with less steric hindrance from having strong reactivity and intense heat release at the beginning of the reaction, which may cause side reactions to occur easily at an excessively high temperature. The reaction is controlled at a lower temperature with the ice-water bath.

In the present disclosure, a purpose of continuing the reaction at 20° C. to 50° C. is that: a secondary amine with larger steric hindrance has weaker reactivity with the thiodiglycolic anhydride. Therefore, raising the reaction temperature to a certain value can accelerate the reaction, thereby increasing the reaction yield.

A third aspect of the present disclosure is to provide use of the thiodiglycolamic acid extractant in extraction of precious metal ions in an acidic feed liquid.

Further, the use is to extract an acidic precious metal feed liquid with an organic phase composed of the thiodiglycolamic acid extractant and a diluent. The use specifically includes the following steps:

(1) dissolving the thiodiglycolamic acid extractant in a diluent to obtain an extractant solution; and (2) mixing the extractant solution obtained in step (1) with an acidic precious metal feed liquid in a constant-temperature oscillator to conduct extraction, such that a precious metal is extracted into the extractant solution to allow for enrichment.

Preferably, in step (1), the diluent is any one or more selected from the group consisting of toluene, dichloromethane, kerosene, and n-heptane.

Preferably, in step (1), the extractant solution has a concentration of 0.05 mol/L to 0.2 mol/L.

Preferably, in step (2), the acidic precious metal feed liquid includes any one or more of gold ions, palladium ions, copper ions, lead ions, cobalt ions, nickel ions, calcium ions, and magnesium ions.

Preferably, in step (2), the acidic precious metal feed liquid has a pH value of 0 to 5.

Preferably, in step (2), the extractant solution and the acidic precious metal feed liquid are at a volume ratio of 1:10.

Preferably, in step (2), the constant-temperature oscillator has an operating temperature of 20° C. to 30° C., more preferably 25° C.

Preferably, in step (2), the constant-temperature oscillator has a rotational speed of 100 rpm to 300 rpm.

In the present disclosure, the thiodiglycolamic acid extractant has desirable extraction ability and high selectivity for precious metal ions under acidic conditions. The extractant can directly and efficiently separate precious metals from a multi-metal system, shortens a process flow of precious metal recovery, and avoids environmental pollution caused by a pre-purification process. The extractant shows an extraction performance significantly better than that of a common thiodiamide extractant, and has a simple and easy-to-operate synthesis method, which is convenient for industrialized production.

Compared with the prior art, the present disclosure has the following beneficial effects:

The present disclosure provides a thiodiglycolamic acid extractant. On one hand, in a structure of the extractant, there are flexibility of an ether-sulfur bond and a coordination effect of sulfur atoms on this bond. This can make an extraction ability of the thiodiglycolamic acid extractant to the precious metal ions much better than that of a common thiodiamide extractant. Moreover, in the structure of the extractant, the active hydrogen in a carboxylic acid functional group can form a hydrogen bond with a solvent to cause solvation, thereby facilitating the dissolution of an extract in the organic phase. Furthermore, the reverse extraction of metal ions can be achieved by controlling the acidity of an aqueous phase. On the other hand, the thiodiglycolamic acid extractant has high selectivity to the precious metal ions, and can directly separate and recover precious metals from an acidic feed liquid. This avoids a pretreatment process of precipitation and impurity removal during the separation and recovery of precious metals by traditional extractants, and overcomes the shortcomings of low comprehensive yield of precious metals and serious environmental pollution. In this way, the separation and recovery of precious metals from the acidic feed liquid is realized with a short process and high efficiency.

DETAILED DESCRIPTION OF THE EMBODIMENTS

Figure 1:
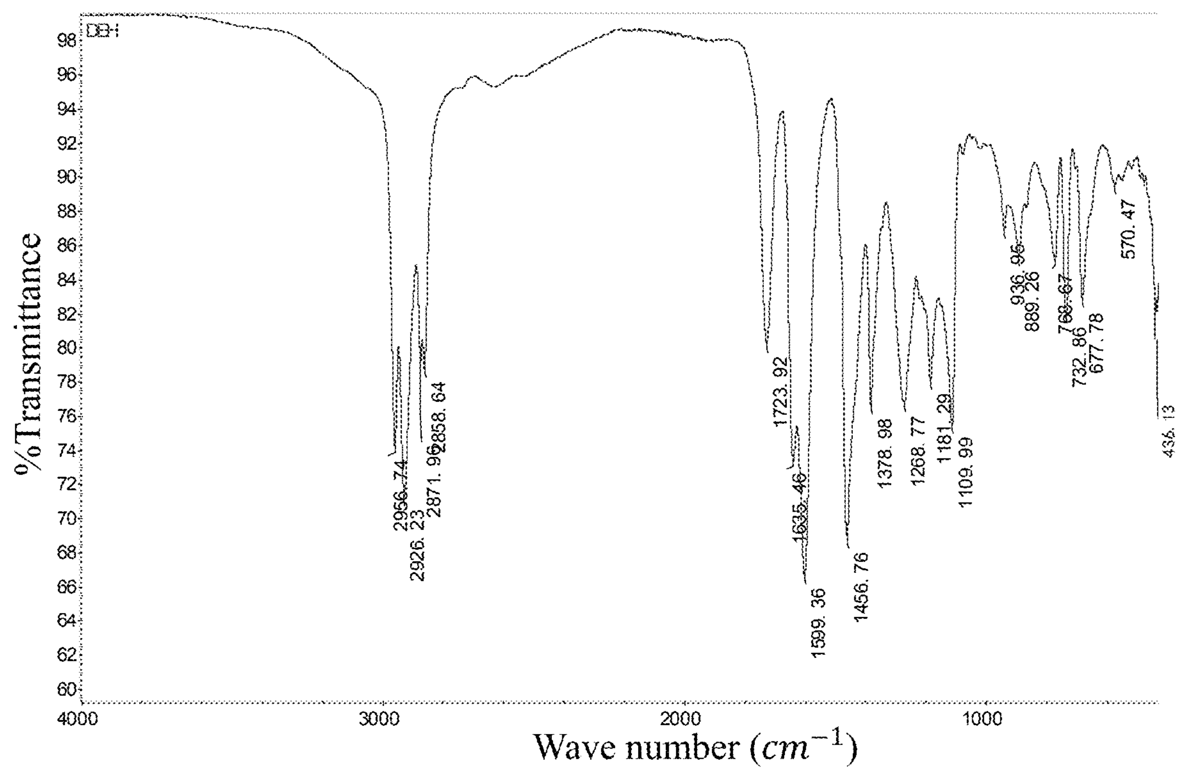
FIG. 1 shows an infrared spectrum of N,N'-diisooctyl-3-thiodiglycolamic acid prepared in Example 1 of the present disclosure.

The present disclosure provides a thiodiglycolamic acid extractant, having a structural formula as follows:

formula 1

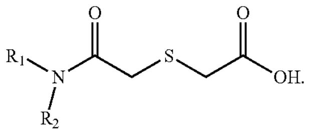

$R_1$ and $R_2$ are independently linear or branched alkyl, and there are totally greater than six, preferably 7 to 24 carbon atoms in $R_1$ and $R_2$.

The present disclosure further provides a preparation method of the thiodiglycolamic acid extractant, including the following steps:

mixing thiodiglycolic anhydride, an alkyl-substituted secondary amine, and an organic reagent in proportion in a 500 mL round-bottom flask; subjecting a resulting mixed reactant to a reaction I by stirring in an ice-water bath for 10 min to 60 min, and then to a reaction II by stirring at 20° C. to 50° C. for 6 h to 24 h; after the reaction II is completed, subjecting an obtained organic phase to washing with a dilute hydrochloric acid solution to remove excess secondary amine, repeated washing with deionized water to a pH value of 3 to 4, drying with anhydrous magnesium sulfate, and vacuum suction filtration; and subjecting an obtained organic phase filtrate to rotary evaporation to remove a solvent, to obtain the thiodiglycolamic acid extractant. The alkyl-substituted secondary amine has a structural formula as follows:

formula 2

where $R_1$ and $R_2$ are independently linear or branched alkyl, and there are totally 7 to 24 carbon atoms in $R_1$ and $R_2$.

The disclosure will be further described in detail in conjunction with examples. The examples are implemented on the premise of the technology of the disclosure, and detailed embodiments and specific operating procedures are now given to illustrate that the disclosure is inventive, but the scope of protection of the disclosure is not limited to the following examples.

In the present disclosure, all equipment and raw materials used are commercially available or are commonly used in the art. All methods in the following examples are conventional methods in the art, unless otherwise specified.

Example 1

In this example, a preparation method of an N,N'-diisooctyl-3-thiodiglycolamic acid extractant included the following steps:

0.2 mmol of thiodiglycolic anhydride, 0.22 mmol of diisooctylamine, and 200 mL of tetrahydrofuran were mixed in a 500 mL round-bottom flask; a resulting mixed reactant was subjected to a reaction I by stirring in an ice-water bath for 30 min, and then to a reaction II by stirring at 40° C. for 24 h; after the reaction II was completed, an obtained organic phase was subjected to washing with a dilute hydrochloric acid solution to remove excess diisooctylamine, followed by washing with deionized water until a pH value was 4, drying with anhydrous magnesium sulfate, and suction filtration; and an obtained organic phase filtrate was subjected to vacuum distillation to remove a solvent, to obtain the N,N'-diisooctyl-3-thiodiglycolamic acid extractant.

Figure 2:
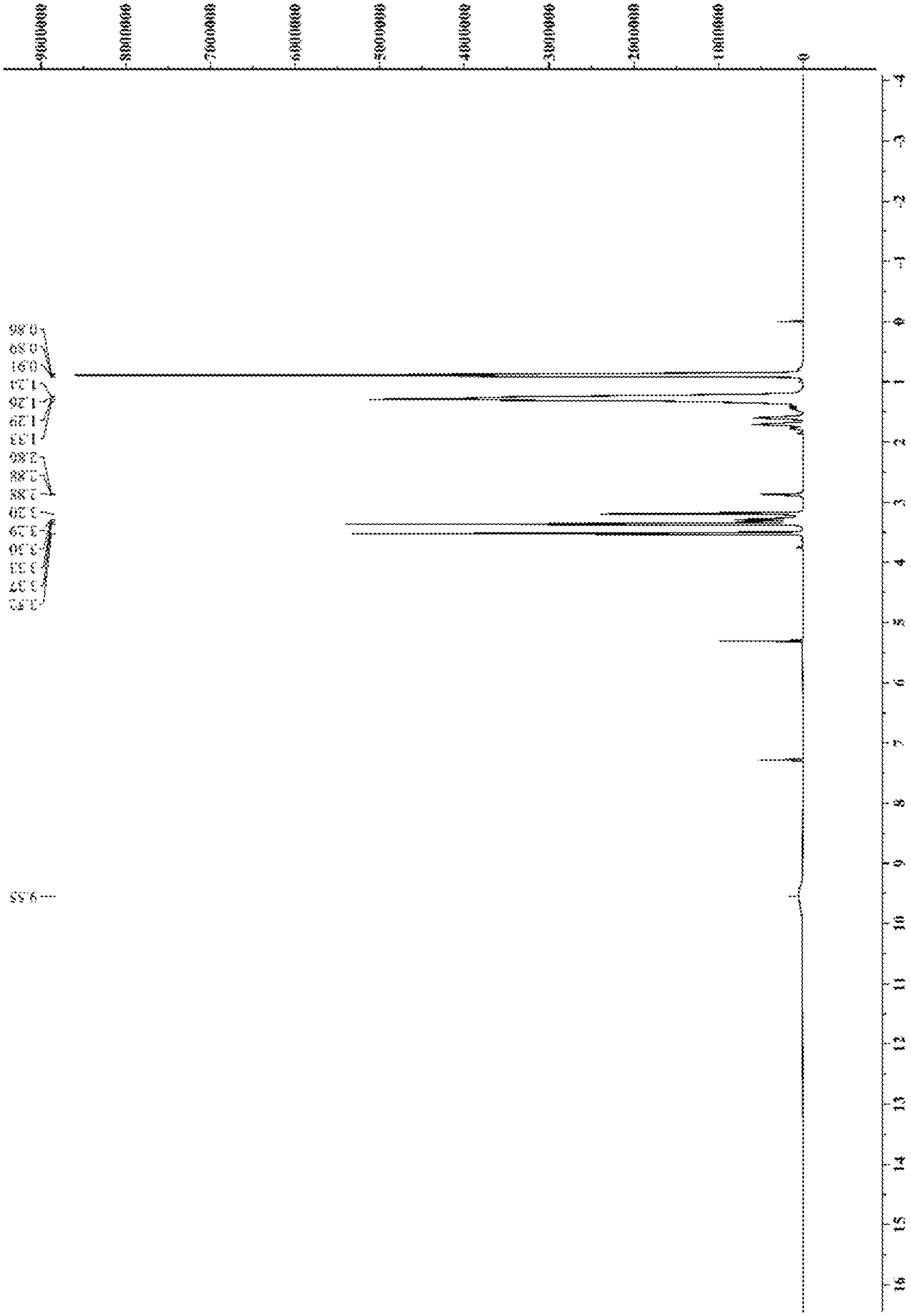
FIG. 2 shows an $^{1}$H-NMR spectrogram of the N,N'-diisooctyl-3-thiodiglycolamic acid prepared in Example 1 of the present disclosure in deuterated chloroform.

The product prepared in this example was characterized, and the results were shown in FIG. 1 to FIG. 2.

FIG. 1 showed an infrared spectrum of the product prepared in Example 1. The main characteristic absorption peak was a peak at 2,926 $cm^{-1}$, indicating that there was stretching vibration of a saturated C—H bond. The peak at 1,723 $cm^{-1}$ was a stretching vibration absorption peak of a C═O bond of the carboxyl, the peak at 1,599 $cm^{-1}$ was a stretching vibration absorption peak of a C═O bond of the amide, the peak at 1,457 $cm^{-1}$ was a stretching vibration absorption peak of a C—N bond of the amide, and the peak at 1,269 $cm^{-1}$ was an asymmetric stretching vibration absorption peak of C—S—C. These characteristic peaks indicated the presence of carboxylic acid, amide, and thioether functional groups.

FIG. 2 showed an 1H-NMR spectrogram of the product prepared in Example 1 in deuterated chloroform. The chemical shifts of each proton were as follows: 9.55 (s, 1H,COOH), 3.52 (s,2H, —$SCH_2$—), 3.37 (s,2H, —$CH_2S$—), 3.20-3.33 (m, 4H, 2×$CH_2$—N), 2.86-2.88 (m, 2H, 2×CH), 1.24-1.33 (m, 16H, 8×$CH_2$), 0.86-0.91 (m, 12H, 4×$CH_3$).

It was known from the data in FIG. 1 and FIG. 2 that the product prepared in Example 1 of the present disclosure was the N,N'-diisooctyl-3-thiodiglycolamic acid.

Example 2

In this example, a preparation method of an N,N'-methyloctyl-3-thiodiglycolamic acid extractant included the following steps:

0.2 mmol of thiodiglycolic anhydride, 0.4 mmol of N-methyloctylamine, and 300 mL of DMF were mixed in a 500 mL round-bottom flask; a resulting mixed reactant was subjected to a reaction I by stirring in an ice-water bath for 30 min, and then to a reaction II by stirring at 20° C. for 24 h; after the reaction II was completed, an obtained organic phase was subjected to washing with a dilute hydrochloric acid solution to remove excess N-methyloctylamine, followed by washing with deionized water until a pH value was 4, drying with anhydrous magnesium sulfate, and suction filtration; and an obtained organic phase filtrate was subjected to vacuum distillation to remove a solvent, to obtain the N,N'-methyloctyl-3-thiodiglycolamic acid extractant.

Figure 3:
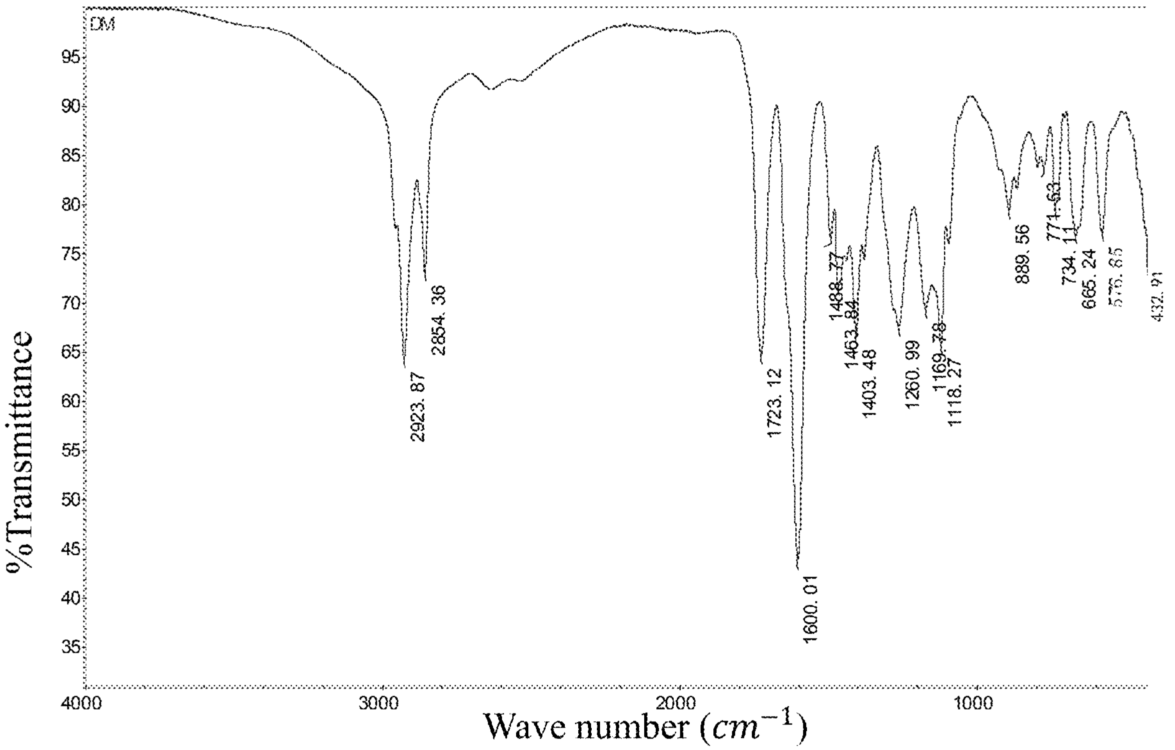
FIG. 3 shows an infrared spectrum of N,N'-methyloctyl-3-thiodiglycolamic acid prepared in Example 2 of the present disclosure.
Figure 4:
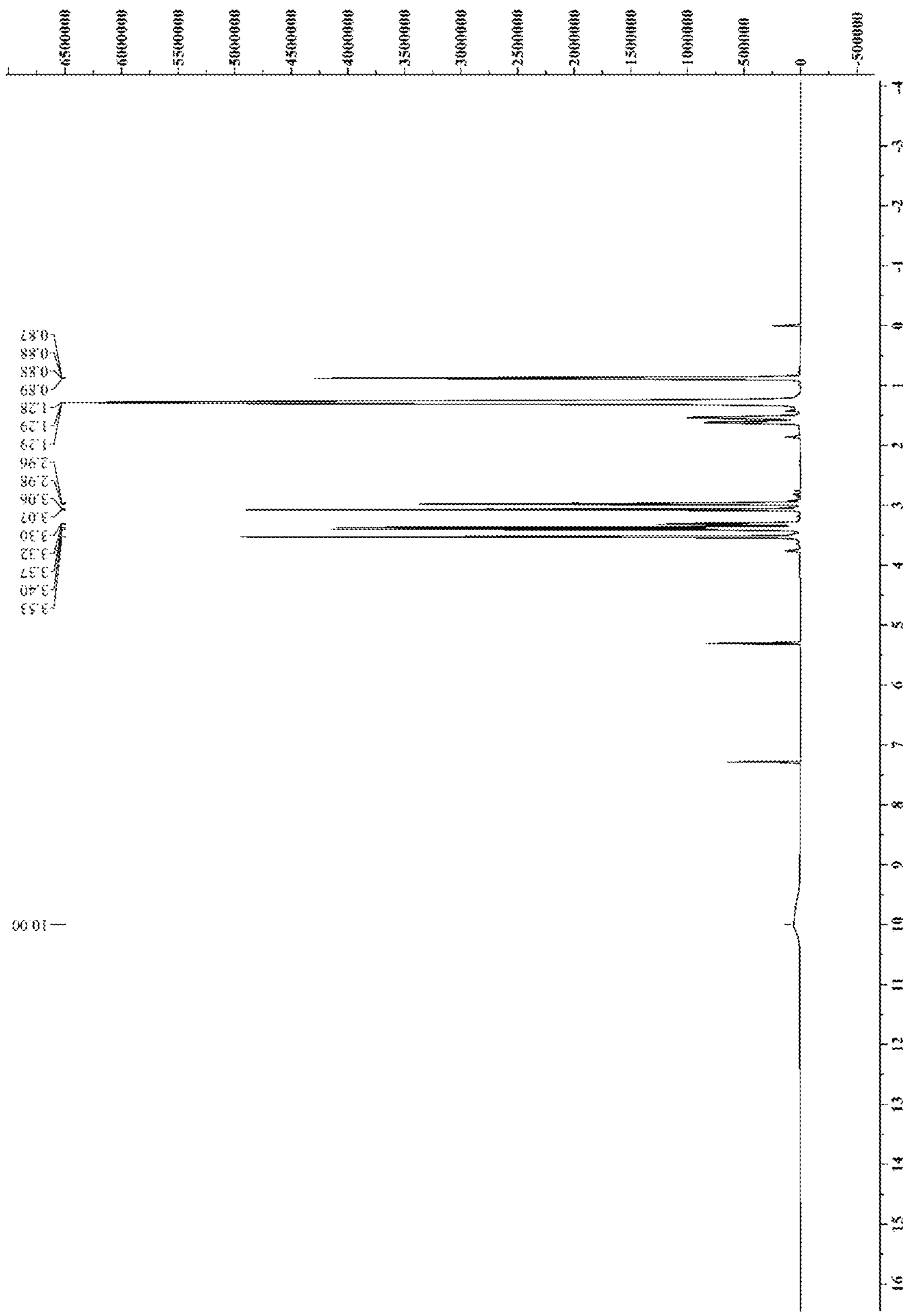
FIG. 4 shows an $^{1}$H-NMR spectrogram of the N,N'-methyloctyl-3-thiodiglycolamic acid prepared in Example 2 of the present disclosure in deuterated chloroform.

The extractant prepared in this example was characterized, and the results were shown in FIG. 3 to FIG. 4.

FIG. 3 showed an infrared spectrum of the product prepared in this example. The main characteristic absorption peak was a peak at 2,924 $cm^{-1}$, indicating that there was stretching vibration of a saturated C—H bond. The peak at 1,723 $cm^{-1}$ was a stretching vibration absorption peak of a C═O bond of the carboxyl, the peak at 1,600 $cm^{-1}$ was a stretching vibration absorption peak of a C═O bond of the amide, the peak at 1,403 $cm^{-1}$ was a stretching vibration absorption peak of a C—N bond of the amide, and the peak at 1,261 $cm^{-1}$ was an asymmetric stretching vibration absorption peak of C—S—C. These characteristic peaks indicated the presence of carboxylic acid, amide, and thioether functional groups.

FIG. 4 showed an $^1$H-NMR spectrogram of the product prepared in this example in deuterated chloroform. The chemical shifts of each proton were as follows: 10.0 (s, 1H, COOH), 3.53 (s,2H, —$SCH_2$—), 3.40 (s, 2H, —$CH_2S$—), 3.30-3.37 (m, 2H, $CH_2$—N), 2.96-3.07 (m, 3H, $CH_3$—N), 1.28-1.29 (m, 8H, 4×$CH_2$), 0.87-0.89 (m, 3H, $CH_3$).

It was known from the data in FIG. 3 and FIG. 4 that the product prepared in this example was the N,N'-methyloctyl-3-thiodiglycolamic acid.

Example 3

In this example, a preparation method of an N,N'-di-n-octyl-3-thiodiglycolamic acid extractant included the following steps:

0.2 mmol of thiodiglycolic anhydride, 0.3 mmol of di-n-octylamine, and 250 mL of dichloromethane were mixed in a 500 mL round-bottom flask; a resulting mixed reactant was subjected to a reaction I by stirring in an ice-water bath for 30 min, and then to a reaction II by stirring at 50° C. for 24 h; after the reaction II was completed, an obtained organic phase was subjected to washing with a dilute hydrochloric acid solution to remove excess di-n-octylamine, followed by washing with deionized water until a pH value was 4, drying with anhydrous magnesium sulfate, and suction filtration; and an obtained organic phase filtrate was subjected to vacuum distillation to remove a solvent, to obtain the N,N'-di-n-octyl-3-thiodiglycolamic acid extractant.

Figure 5:
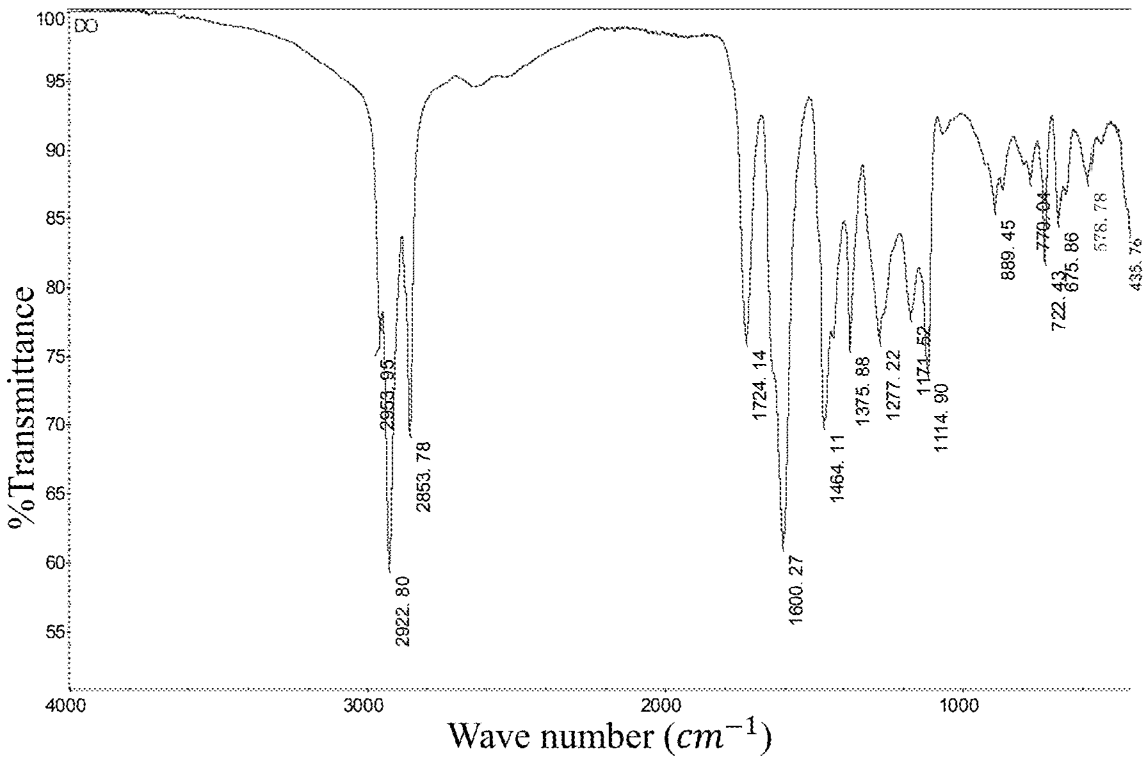
FIG. 5 shows an infrared spectrum of N,N'-di-n-octyl-3-thiodiglycolamic acid prepared in Example 3 of the present disclosure.
Figure 6:
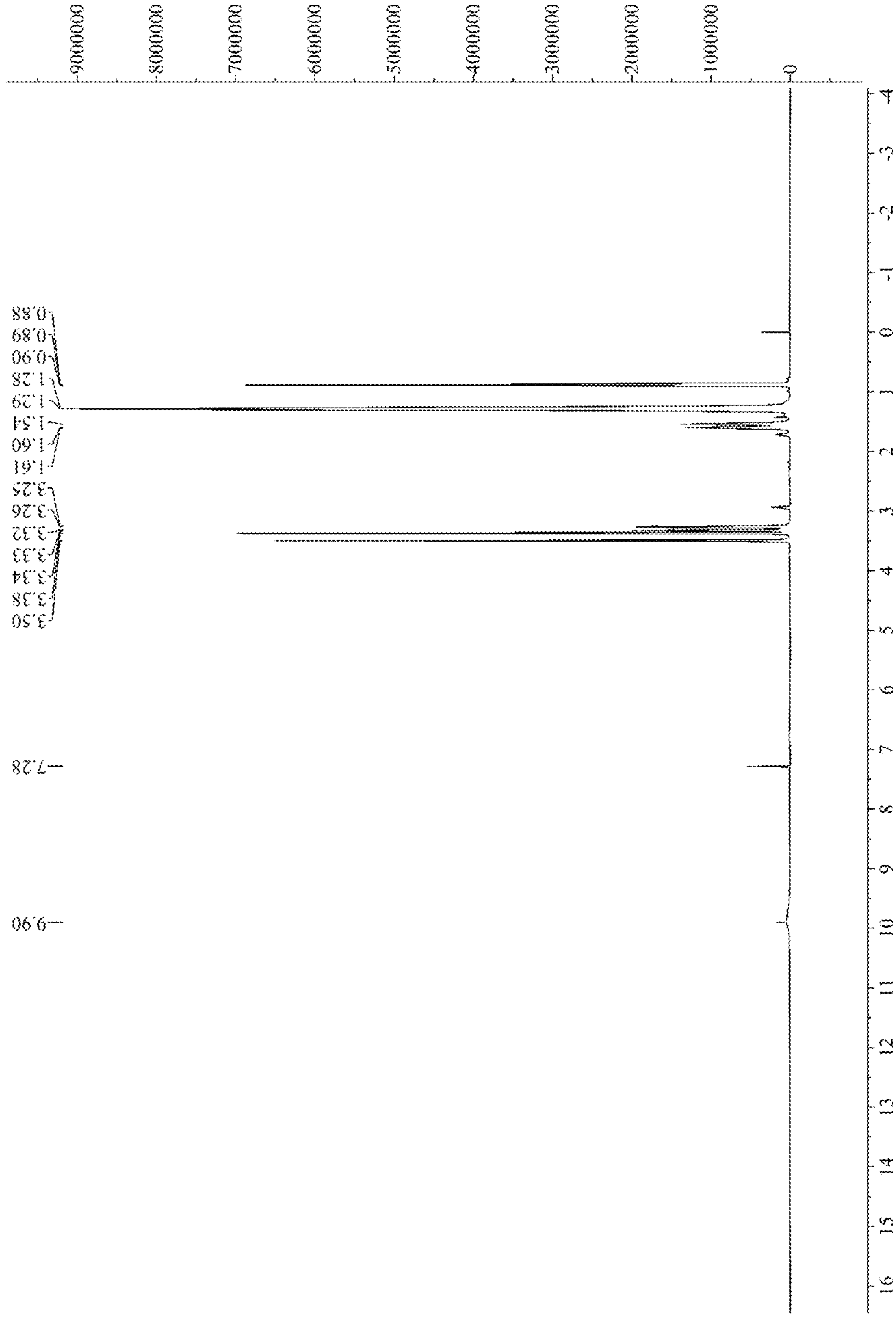
FIG. 6 shows an $^1$H-NMR spectrogram of the N,N'-di-n-octyl-3-thiodiglycolamic acid prepared in Example 3 of the present disclosure in deuterated chloroform.

The extractant prepared in this example was characterized, and the results were shown in FIG. 5 to FIG. 6.

FIG. 5 showed an infrared spectrum of the product prepared in Example 3. The main characteristic absorption peak was a peak at 2,923 $cm^{-1}$, indicating that there was stretching vibration of a saturated C—H bond. The peak at 1,724 $cm^{-1}$ was a stretching vibration absorption peak of a C═O bond of the carboxyl, the peak at 1,600 $cm^{-1}$ was a stretching vibration absorption peak of a C═O bond of the amide, the peak at 1,464 $cm^{-1}$ was a stretching vibration absorption peak of a C—N bond of the amide, and the peak at 1,277 $cm^{-1}$ was an asymmetric stretching vibration absorption peak of C—S—C. These characteristic peaks indicated the presence of carboxylic acid, amide, and thioether functional groups.

FIG. 6 showed an 1H-NMR spectrogram of the product prepared in Example 3 in deuterated chloroform. The chemical shifts of each proton were as follows: 9.9(s, 1H, COOH), 3.50 (s, 2H, —$SCH_2$—), 3.38 (s, 2H, —$CH_2S$—), 3.25-3.34 (m, 4H, 2×$CH_2$—N), 1.54-1.61 (m, 4H, 2×-$CH_2CH_2$—N), 1.28-1.29 (m, 10H, 5×$CH_2$), 0.88-0.90 (m, 6H, 2×$CH_3$).

It was known from the data in FIG. 5 and FIG. 6 that the product prepared in this example was the N,N'-di-n-octyl-3-thiodiglycolamic acid.

Example 4

In this example, a preparation method of an N,N'-di-n-hexyl-3-thiodiglycolamic acid extractant included the following steps:

0.2 mmol of thiodiglycolic anhydride, 0.2 mmol of di-n-hexylamine, and 200 mL of chloroform were mixed in a 500 mL round-bottom flask; a resulting mixed reactant was subjected to a reaction I by stirring in an ice-water bath for 30 min, and then to a reaction II by stirring at 30° C. for 24 h; after the reaction II was completed, an obtained organic phase was subjected to washing with a dilute hydrochloric acid solution to remove excess di-n-hexylamine, followed by washing with deionized water until a pH value was 4, drying with anhydrous magnesium sulfate, and suction filtration; and an obtained organic phase filtrate was subjected to vacuum distillation to remove a solvent, to obtain the N,N'-di-n-hexyl-3-thiodiglycolamic acid extractant.

Figure 7:
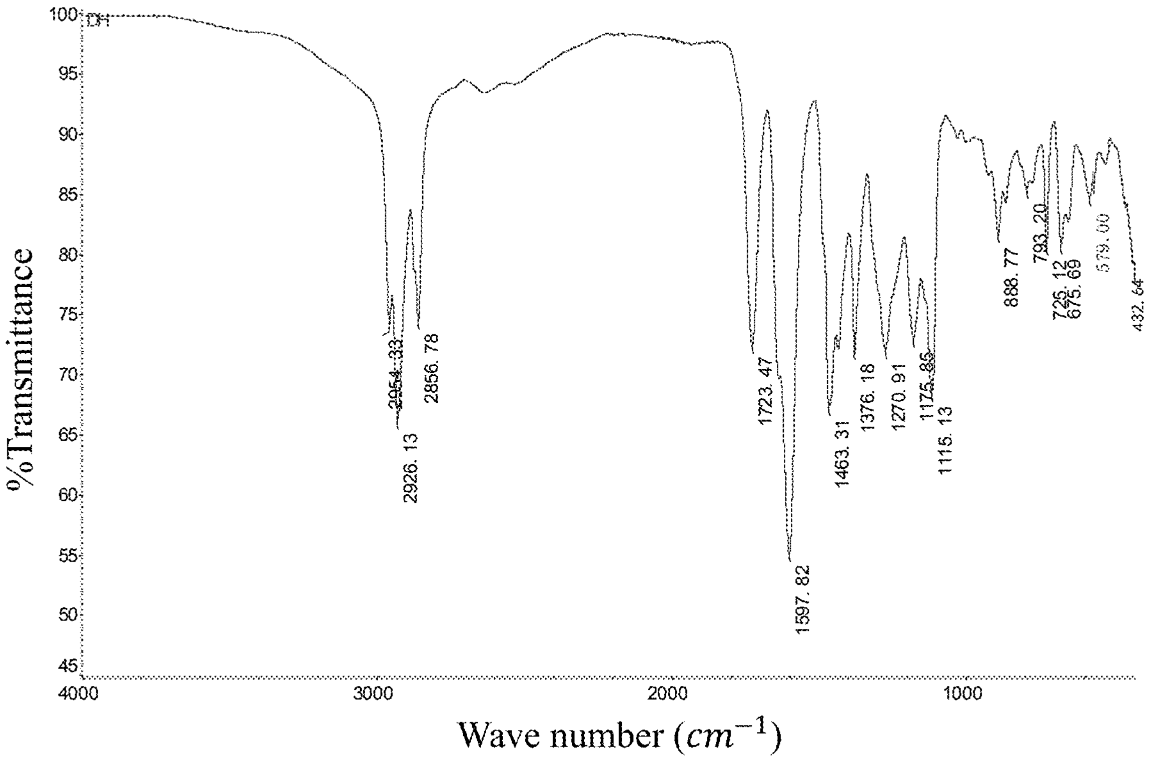
FIG. 7 shows an infrared spectrum of N,N'-di-n-hexyl-3-thiodiglycolamic acid prepared in Example 4 of the present disclosure.
Figure 8:
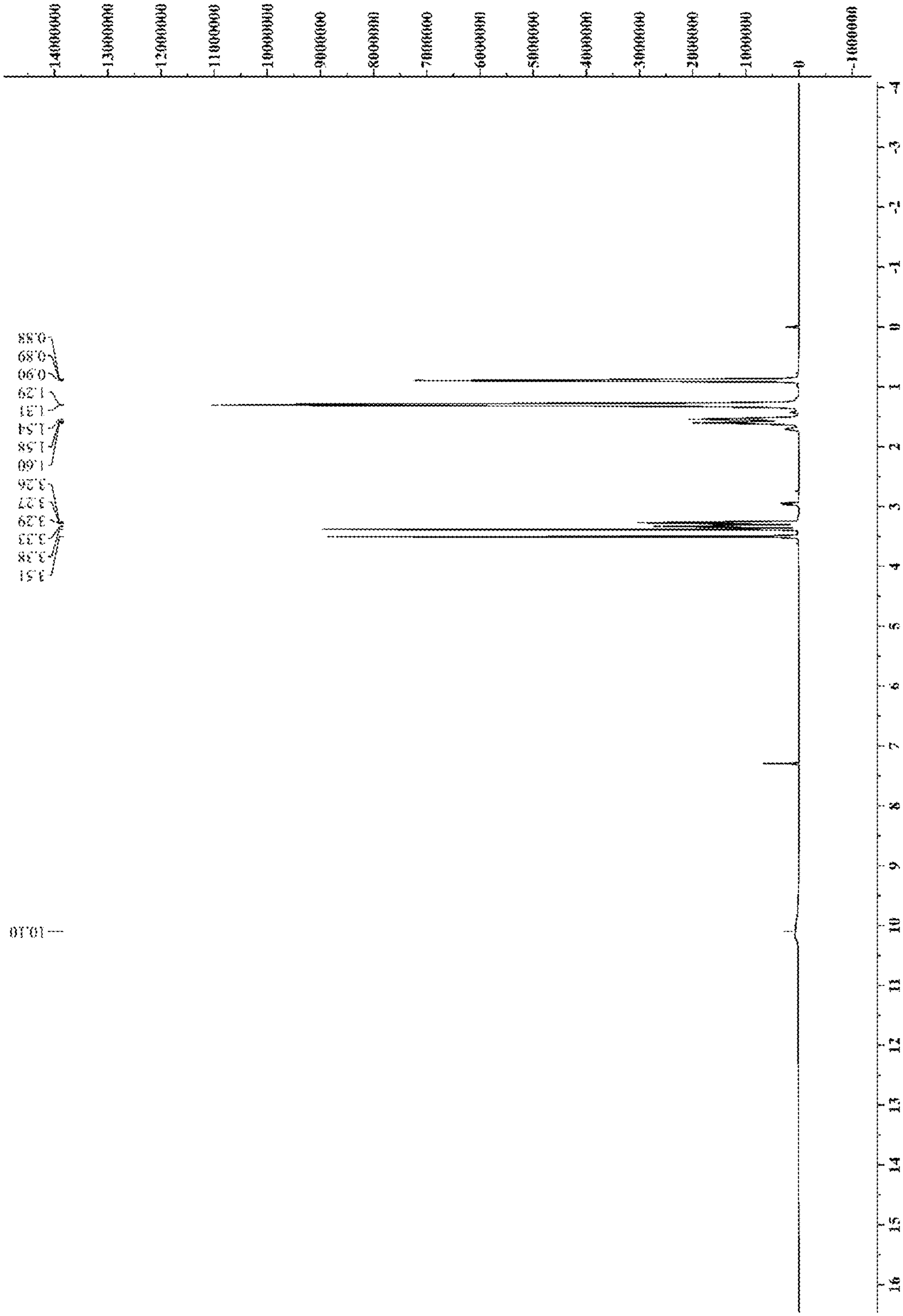
FIG. 8 shows an $^1$H-NMR spectrogram of the N,N'-di-n-hexyl-3-thiodiglycolamic acid prepared in Example 4 of the present disclosure in deuterated chloroform.

The product prepared in this example was characterized, and the results were shown in FIG. 7 to FIG. 8.

FIG. 7 showed an infrared spectrum of the product prepared in Example 4. The main characteristic absorption peak was a peak at 2,926 $cm^{-1}$, indicating that there was stretching vibration of a saturated C—H bond. The peak at 1,723 $cm^{-1}$ was a stretching vibration absorption peak of a C═O bond of the carboxyl, the peak at 1,598 $cm^{-1}$ was a stretching vibration absorption peak of a C═O bond of the amide, the peak at 1,463 $cm^{-1}$ was a stretching vibration absorption peak of a C—N bond of the amide, and the peak at 1,271 $cm^{-1}$ was an asymmetric stretching vibration absorption peak of C—S—C. These characteristic peaks indicated the presence of carboxylic acid, amide, and thioether functional groups.

FIG. 8 showed an $^1$H-NMR spectrogram of the product prepared in Example 4 in deuterated chloroform. The chemical shifts of each proton were as follows: 10.1 (s, 1H, COOH), 3.51 (s, 2H, —$SCH_2$—), 3.38 (s, 2H, —$CH_2S$—), 3.26-3.33 (m, 4H, 2×$CH_2$—N), 1.54-1.60 (m, 4H, 2×-$CH_2CH_2$—N), 1.29-1.31 (m, 6H, 3×$CH_2$), 0.88-0.90 (m, 6H, 2×$CH_3$).

It was known from the data in FIG. 7 and FIG. 8 that the product prepared in this example was the N,N'-di-n-hexyl-3-thiodiglycolamic acid.

USE EXAMPLE

Each of the extractants prepared in the above examples of the present disclosure were used to extract precious metal ions in an acidic feed liquid.

In the following use examples, a precious metal feed liquid had the same composition, specifically including: gold ions, palladium ions, copper ions, lead ions, cobalt ions, nickel ions, calcium ions, and magnesium ions. Each type of the metal ions had a concentration of 100 mg/L. A configuration method of the feed liquid included: a standard solution of each metal ion with a concentration of 1,000 mg/L was diluted in a volumetric flask, and then the pH value of a resulting diluted solution was adjusted with a 0.5 mol/L HCl solution and a 0.5 mol/L NaOH solution, to obtain precious metal feed liquids with different pH values.

A calculation method of an extraction rate involved in each of the following use examples was as follows:

the extraction rate was represented by E (%), $$E = \frac{C_0 - C_e}{C_0} \times 100\%;$$

where $C_0$: a metal ion concentration in an initial aqueous solution (mg/L); and $C_e$: a metal ion concentration in an aqueous phase after extraction equilibrium (mg/L).

Use Example 1

The N,N'-methyloctyl-3-thiodiglycolamic acid extractant prepared in Example 2 was used to extract precious metal ions in an acidic feed liquid. A specific use method included the following steps:

2.75 g of the N,N'-methyloctyl-3-thiodiglycolamic acid extractant prepared in Example 2 was dissolved in kerosene to obtain a 0.1 mol/L extractant solution; and the 0.1 mol/L extractant solution and a precious metal feed liquid with a pH value of 1.03 were mixed in a constant-temperature oscillator at a volume ratio of 1:10, and subjected to extraction by oscillating at 230 rpm and a constant temperature of 25° C. for 15 min; concentrations of metal ions in an aqueous phase were determined before and after the extraction, and an extraction rate of each metal ion was calculated. The specific results were shown in Table 1.

Use Example 2

The N,N'-di-n-hexyl-3-thiodiglycolamic acid extractant prepared in Example 4 was used to extract precious metal ions in an acidic feed liquid. A specific use method included the following steps:

3.18 g of the N,N'-di-n-hexyl-3-thiodiglycolamic acid extractant prepared in Example 4 was dissolved in kerosene to obtain a 0.1 mol/L extractant solution; and the 0.1 mol/L extractant solution and a precious metal feed liquid with a pH value of 1.03 were mixed in a constant-temperature oscillator at a volume ratio of 1:10, and subjected to extraction by oscillating at 230 rpm and a constant temperature of 25° C. for 15 min; concentrations of metal ions in an aqueous phase were determined before and after the extraction, and an extraction rate of each metal ion was calculated. The specific results were shown in Table 1.

Use Example 3

The N,N'-diisooctyl-3-thiodiglycolamic acid extractant prepared in Example 1 was used to extract precious metal ions in an acidic feed liquid. A specific use method included the following steps:

3.74 g of the N,N'-diisooctyl-3-thiodiglycolamic acid extractant prepared in Example 1 was dissolved in kerosene to obtain a 0.1 mol/L extractant solution; and the 0.1 mol/L extractant solution and a precious metal feed liquid with a pH value of 1.03 were mixed in a constant-temperature oscillator at a volume ratio of 1:10, and subjected to extraction by oscillating at 230 rpm and a constant temperature of 25° C. for 15 min; concentrations of metal ions in an aqueous phase were determined before and after the extraction, and an extraction rate of each metal ion was calculated. The specific results were shown in Table 1.

Use Example 4

The N,N'-di-n-octyl-3-thiodiglycolamic acid extractant prepared in Example 3 was used to extract precious metal ions in an acidic feed liquid. A specific use method included the following steps:

3.74 g of the N,N'-di-n-octyl-3-thiodiglycolamic acid extractant was dissolved in kerosene to obtain a 0.1 mol/L extractant solution; and the 0.1 mol/L extractant solution and a precious metal feed liquid with a pH value of 1.03 were mixed in a constant-temperature oscillator at a volume ratio of 1:10, and subjected to extraction by oscillating at 230 rpm and a constant temperature of 25° C. for 15 min; concentrations of metal ions in an aqueous phase were determined before and after the extraction, and an extraction rate of each metal ion was calculated. The specific results were shown in Table 1.

TABLE 1

Comparison of extraction rate results in Use Examples 1 to 4

| | E (%) | | | | | | | |
|---|---|---|---|---|---|---|---|---|
| Use Example | Au | Pd | Cu | Pb | Co | Ni | Ca | Mg |
| Use Example 1 | 86.68 | 99.47 | 10.21 | 8.21 | 10.08 | 10.74 | 0 | 16.87 |
| Use Example 2 | 91.79 | 99.68 | 8.14 | 4.09 | 9.23 | 9.61 | 0 | 13.59 |
| Use Example 3 | 98.32 | 99.93 | 6.55 | 1.41 | 8.55 | 8.77 | 0 | 12.5 |
| Use Example 4 | 99.98 | 99.95 | 0.86 | 0 | 7.63 | 8.09 | 0 | 9.88 |

It was seen from the results in Table 1 that the longer a carbon chain substituted on the nitrogen atom in an extractant structure was, the higher the extraction rate of precious metal ions could be. Moreover, the higher the degree of branching of the carbon chain of the substituted alkyl was, the lower the extraction rate of precious metal ions could be. The reason was that as the carbon chain of the alkyl substituting on the nitrogen atom in the extractant structure grew, the stability of an extract compound formed between the extractant and the metal ions during the extraction was higher. This was beneficial to the extraction. However, the higher the degree of branching of the carbon chain of the substituted alkyl was, the greater the steric hindrance between the extractant and the metal ions could be, and was more unfavorable for the formation of the extract. Therefore, the extraction rate of metal ions decreased.

Use Example 5

The N,N'-diisooctyl-3-thiodiglycolamic acid extractant prepared in Example 1 was used to extract precious metal ions in an acidic feed liquid. A specific use method included the following steps:

7.48 g of the N,N'-diisooctyl-3-thiodiglycolamic acid extractant prepared in Example 1 was dissolved in kerosene to obtain a 0.2 mol/L extractant solution; and the 0.2 mol/L extractant solution and a precious metal feed liquid with a pH value of 1.03 were mixed in a constant-temperature oscillator at a volume ratio of 1:10, and subjected to extraction by oscillating at 230 rpm and a constant temperature of 25° C. for 15 min; concentrations of metal ions in an aqueous phase were determined before and after the extraction, and an extraction rate of each metal ion was calculated. The specific results were shown in Table 2.

Use Example 6

The N,N'-diisooctyl-3-thiodiglycolamic acid extractant prepared in Example 1 was used to extract precious metal ions in an acidic feed liquid. A specific use method included the following steps:

7.48 g of the N,N'-diisooctyl-3-thiodiglycolamic acid extractant was dissolved in kerosene to obtain a 0.2 mol/L extractant solution; and the 0.2 mol/L extractant solution and a precious metal feed liquid with a pH value of 0.3 were mixed in a constant-temperature oscillator at a volume ratio of 1:10, and subjected to extraction by oscillating at 230 rpm and a constant temperature of 25° C. for 15 min; concentrations of metal ions in an aqueous phase were determined before and after the extraction, and an extraction rate of each metal ion was calculated. The specific results were shown in Table 2.

Use Example 7

The N,N'-diisooctyl-3-thiodiglycolamic acid extractant prepared in Example 1 was used to extract precious metal ions in an acidic feed liquid. A specific use method included the following steps:

7.48 g of the N,N'-diisooctyl-3-thiodiglycolamic acid extractant was dissolved in kerosene to obtain a 0.2 mol/L extractant solution; and the 0.2 mol/L extractant solution and a precious metal feed liquid with a pH value of 2.43 were mixed in a constant-temperature oscillator at a volume ratio of 1:10, and subjected to extraction by oscillating at 230 rpm and a constant temperature of 25° C. for 15 min; concentrations of metal ions in an aqueous phase were determined before and after the extraction, and an extraction rate of each metal ion was calculated. The specific results were shown in Table 2.

Use Example 8

The N,N'-diisooctyl-3-thiodiglycolamic acid extractant prepared in Example 1 was used to extract precious metal ions in an acidic feed liquid. A specific use method included the following steps:

- 7.48 g of the N,N'-diisooctyl-3-thiodiglycolamic acid extractant was dissolved in kerosene to obtain a 0.2 mol/L extractant solution; and
- the 0.2 mol/L extractant solution and a precious metal feed liquid with a pH value of 3.2 were mixed in a constant-temperature oscillator at a volume ratio of 1:10, and subjected to extraction by oscillating at 230 rpm and a constant temperature of 25° C. for 15 min; concentrations of metal ions in an aqueous phase were determined before and after the extraction, and an extraction rate of each metal ion was calculated. The specific results were shown in Table 2.

Use Example 9

The N,N'-diisooctyl-3-thiodiglycolamic acid extractant prepared in Example 1 was used to extract precious metal ions in an acidic feed liquid. A specific use method included the following steps:

- 7.48 g of the N,N'-diisooctyl-3-thiodiglycolamic acid extractant was dissolved in kerosene to obtain a 0.2 mol/L extractant solution; and
- the 0.2 mol/L extractant solution and a precious metal feed liquid with a pH value of 4.05 were mixed in a constant-temperature oscillator at a volume ratio of 1:10, and subjected to extraction by oscillating at 230 rpm and a constant temperature of 25° C. for 15 min; concentrations of metal ions in an aqueous phase were determined before and after the extraction, and an extraction rate of each metal ion was calculated. The specific results were shown in Table 2.

TABLE 2

Comparison of extraction rate results in Use Examples 5 to 9

| | E (%) | | | | | | | |
|---|---|---|---|---|---|---|---|---|
| Use Example | Au | Pd | Cu | Pb | Co | Ni | Ca | Mg |
| Use Example 5 | 99.25 | 99.97 | 7.14 | 2.06 | 18.14 | 18.42 | 0 | 25.02 |
| Use Example 6 | 94.73 | 98.95 | 9.27 | 4.91 | 20.10 | 20.67 | 0 | 25.97 |
| Use Example 7 | 99.78 | 100 | 5.41 | 0 | 18.85 | 18.99 | 0 | 23.04 |
| Use Example 8 | 99.98 | 100 | 3.28 | 0 | 18.71 | 18.89 | 0 | 23.06 |
| Use Example 9 | 100 | 100 | 2.12 | 0 | 15.39 | 15.65 | 0 | 21.37 |

As shown in the results of Table 2, the N,N'-diisooctyl-3-thiodiglycolamic acid extractants of Use Examples 5 to 9 had an extraction rate of precious metals increased with an increase of the pH value, and had an extraction rate of base metals decreased with the increase of the pH value. Therefore, the precious metals could be effectively separated from the base metals by adjusting an appropriate pH value.

The above are merely preferred implementations of the present disclosure. It should be noted that several improvements and modifications may further be made by a person of ordinary skill in the art without departing from the principle of the present disclosure, and such improvements and modifications should also be deemed as falling within the protection scope of the present disclosure.

What is claimed is:

1. A use method of a thiodiglycolamic acid extractant in extraction of metal ions selected from the group consisting of gold ions, palladium ions, copper ions, lead ions, cobalt ions, nickel ions, calcium ions, and magnesium ions in an acidic metal feed liquid, comprising the following steps:

(1) dissolving the thiodiglycolamic acid extractant in a diluent to obtain an extractant solution; and (2) mixing the extractant solution obtained in step (1) with the acidic metal feed liquid in a constant-temperature oscillator to conduct extraction, such that the metal ions are extracted into the extractant solution to allow for enrichment;

wherein the thiodiglycolamic acid extractant has a structural formula shown in formula 1:

formula 1

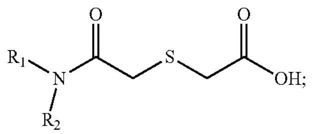

wherein in formula 1, $R_1$ and $R_2$ are independently linear or branched alkyl, and there are totally greater than six carbon atoms in $R_1$ and $R_2$.

2. The use method according to claim 1, wherein in step (1), the diluent is one or more selected from the group consisting of toluene, dichloromethane, kerosene, and n-heptane.

3. The use method according to claim 2, wherein in step (2), the extractant solution and the acidic metal feed liquid are at a volume ratio of 1:10.

4. The use method according to claim 1, wherein in step (1), the extractant solution has a concentration of 0.05 mol/L to 0.2 mol/L.

5. The use method according to claim 1, wherein in step (2), the acidic precious metal feed liquid has a pH value of 0 to 5.

6. The use method according to claim 1, wherein in step (2), the constant-temperature oscillator has an operating temperature of 20° C. to 30° C.

7. The use method according to claim 1, wherein in step (2), the constant-temperature oscillator has a rotational speed of 100 rpm to 300 rpm.

* * * * *